United States

Hsu

4,018,084

Apr. 19, 1977

[54] ACOUSTIC EMISSIONS SIMULATOR

[75] Inventor: Nelson N. Hsu, Lexington, Ky.

[73] Assignee: Lockheed Aircraft Corporation, Burbank, Calif.

[22] Filed: May 13, 1976

[21] Appl. No.: 686,071

[52] U.S. Cl. .............................................. 73/71.5 R
[51] Int. Cl.² ....................................... G01N 29/00
[58] Field of Search ................... 73/71.5 R, 552, 69, 73/1 DV

[56] References Cited

OTHER PUBLICATIONS

Breckenridge et al., *Acoustical Society of America Journal*, vol. 57, No. 3, Mar. 1975, pp. 626–631.

*Primary Examiner*—James J. Gill
*Assistant Examiner*—Anthony V. Ciarlante
*Attorney, Agent, or Firm*—Billy G. Corber; John J. Sullivan

[57] ABSTRACT

This device generates a simulated acoustic emission signal and simultaneously introduces the signal into a test article. The device provides a means for positioning precision brittle tubes or rods against the test article in a controlled fashion. A simulated signal, a stress pulse, is introduced into the test article at a point source when sufficient force is applied to break the tubes or rod against the test article. The stress pulse is generated by the rapid release of elastic energy within the test article itself therefore it very closely simulates the acoustic emission signal generated by a flaw in the material.

7 Claims, 3 Drawing Figures

ACOUSTIC EMISSIONS SIMULATOR

This invention relates to devices for generating a stress pulse of such intensity, form, and duration on a selected, localized area of a metal specimen so as to simulate the acoustic emission which emanates from an actual crack in that specimen.

Acoustic emission techniques have been employed to monitor structural integrity of metal. These monitors, in essence, listen for, detect and transmit or register acoustic emissions which emanate from cracks as they occur in the metal under surveillance. In this way the structural integrity of the metal during service is constantly evaluated and its life span predicted to the point that failures are avoided.

One of the problems in the use of the acoustic emission techniques is the difficulty of producing, at an arbitrarily selected location, a standard acoustic emission in the form of a short duration pulse of controllable amplitude. This standard emission source is employed to calibrate sensors and amplifiers, as well as to verify the operation of the signal processing system, such as determining the source location by triangulation.

Generally considered to be the best of the presently available devices to generate standard emission sources are those which employ: (1) spark impact, (2) ball-bearing dropping on the specimen, (3) ultrasonic transmitters, (4) magnetostrictive transducer driving a wire delay line with a needle-point, and (5) martensitic phase transformations. Among these, the spark impact technique has the advantage of being incorporated in a portable device which generates a producible point source, if both the gap width to produce the spark and the distance from the spark to the specimen are precisely controlled. It also has disadvantages. For example, it cannot be used on certain structure due to the possible fire hazards. Similarly, each of the techniques mentioned above has certain merits and certain limitations; all of these as well as other of the known present day devices are complicated and expensive.

Previous attempts to improve known techniques to generate standard acoustic emission sources have not met with any appreciable success. For example, attempts have been made to modify the ball-bearing dropping technique by using a solenoid driven hammer with a ball-bearing attached to the end of the hammer or using a machinist's automatic punch to drive a ball, but the results lack consistency. Besides in order to simulate the acoustic emission from a crack extension, it is believed, the ball used in these devices must be isolated and of small size (less than one millimeter). Otherwise, the spectrum of the acoustic pulse produced is centered at too low a frequency to simulate that of a crack. Also, double lever beam stress corrosion specimens rigidly attached to dynamic structures, to wit aircraft, have been suggested as an acoustic emission source. This technique lacks mobility and cannot be precisely controlled in time domain because the crack growth in a stress corrosion specimen is a spontaneous event. Moreover, the source location of the emission from a stress corrosion specimen cannot be pinpointed by the plane triangulation method because the size of the specimen and the way it is attached to the structure add one extra dimension to the plane configuration and thus confuse the signal processing system.

Recently, it has been discovered that the breaking of a standard glass capillary tube can be employed as a reproducible acoustic emission standard source for calibrating sensors. In an article in *Journal Acoustical Society of America*, Vol. 57, No. 3, pages 626–631, Mar. 1975 the authors describe the use of a short length of thin-walled glass tube with a diameter of about 0.15 millimeter slowly compressed until it broke to produce a stress pulse with the rise time less than 0.1 microsecond.

The present invention was conceived in the light of the foregoing state of the art, first verifying the results obtained when using the standard glass capillary tube of 0.15 millimeter diameter. Thus it was recognized that the breaking glass tube would be an excellent calibration source provided the breaking process could be carried out in the proper manner with uncomplicated equipment.

To this end a specially designed and constructed tool is proposed which is completely self-contained, i.e., portable and readily manipulatable by the user. This tool is a tapered or pointed cylindrical shaped instrument or pencil adapted to contain a plurality of relatively strong frangible elements or brittle rods such as for example glass tubes of selected diameter. Internally this pencil includes a core having a gripping element to secure one frangible element or glass rod at a time and an actuator operable to advance the secured element a precise distance outwardly of the pointed end of the pencil where it can be placed against the specimen or metal under test. Externally the pencil carries an angularly adjustable support to accurately incline and position the projecting end of the frangible element or glass tube on and against the metal specimen and a deflector adjacent its pointed end to overlie the projecting tube end when so positioned to retain the scatter of glass when the tube is broken.

The simulated acoustic emission signal, the stress pulse, has two unique features which none of the other simulated signals have: 1. The stress pulse generated is through a slow buildingup of the stress field due to localized stress concentration and a rapid release due to the sudden breaking of the frangible element (The phenomenon is more akin to actual acoustic emission than simulations produced by impact type or transducer type devices.); and 2. The form (or the vibration mode) of the stress pulse can be controlled and varied by changing the angle of inclination. Both normal and tangential components of any chosen ratio can be generated simultaneously. Consequently, acoustic emission generated from cracks of arbitrary orientation can be simulated.

Thus, an acoustic emissions simulator is contemplated which offers several additional advantages over prior devices and mechanisms including:

1. it is inexpensive and convenient to use;
2. the acoustic emission can be generated at a pin point location;
3. it can be repeatedly and precisely operated;
4. it is directly pressed on the metal specimen requiring no coupling agent and thus has no adverse effects inherent with coupling agents, such as variation in attenuation, ambiguity in location, and change of boundary conditions of the specimen;
5. it is uncomplicated requiring no wiring and no power supply;
6. the frequency spectrum (signature) of the stress pulse generated can be selectively set by using different sizes of frangible elements, e.g., 0.3 mm, 0.5 mm, 0.7 mm, etc.

With the above and other objects in view as will become apparent this invention consists in the construction, combination and arrangement of parts all as hereinafter more fully described, claimed and illustrated in the accompanying drawings, wherein:

Figure 1:
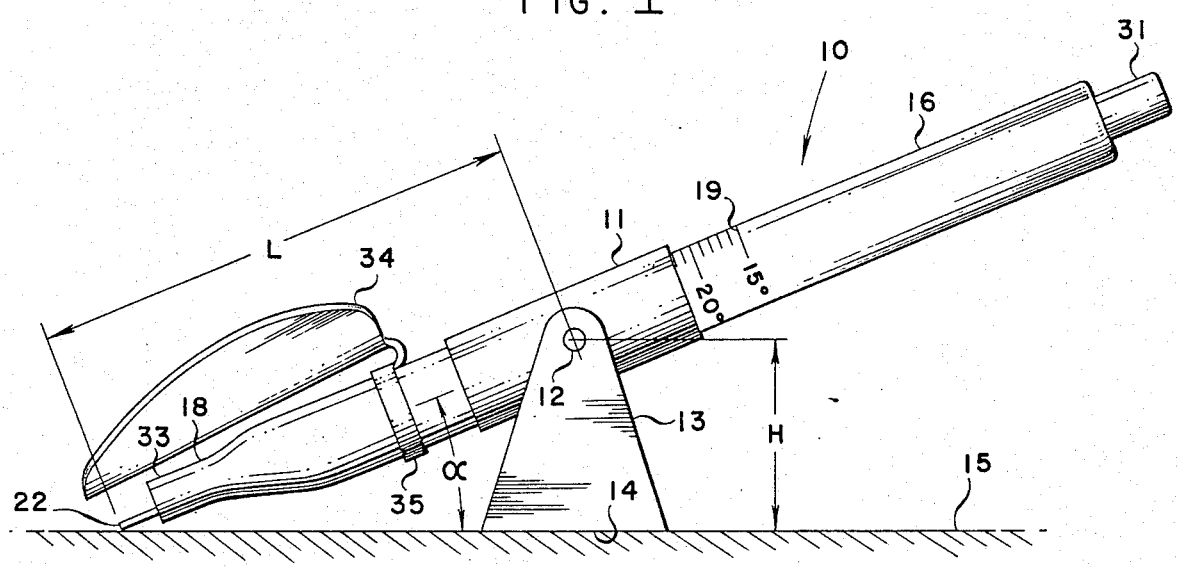
FIG. 1 is a side elevation of an acoustic emissions simulator in accordance with the teachings of this invention showing it in position on a metal test specimen with the glass rod or tube disposed at a selected angle relative to the surface of the specimen.
Figure 2:
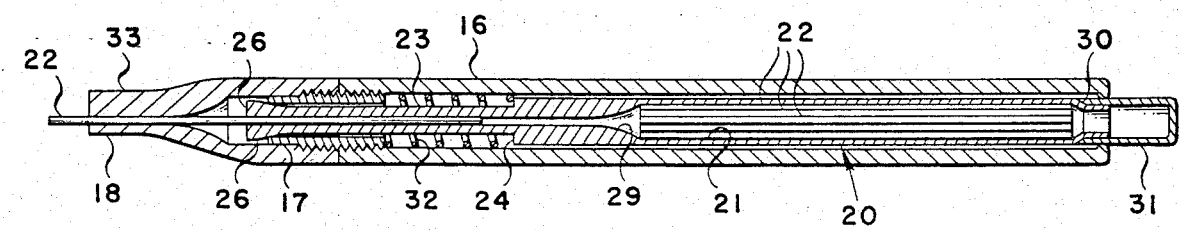
FIG. 2 is a longitudinal section taken through the instrument or pencil of FIG. 1 to show the several internal components thereof.
Figure 3:
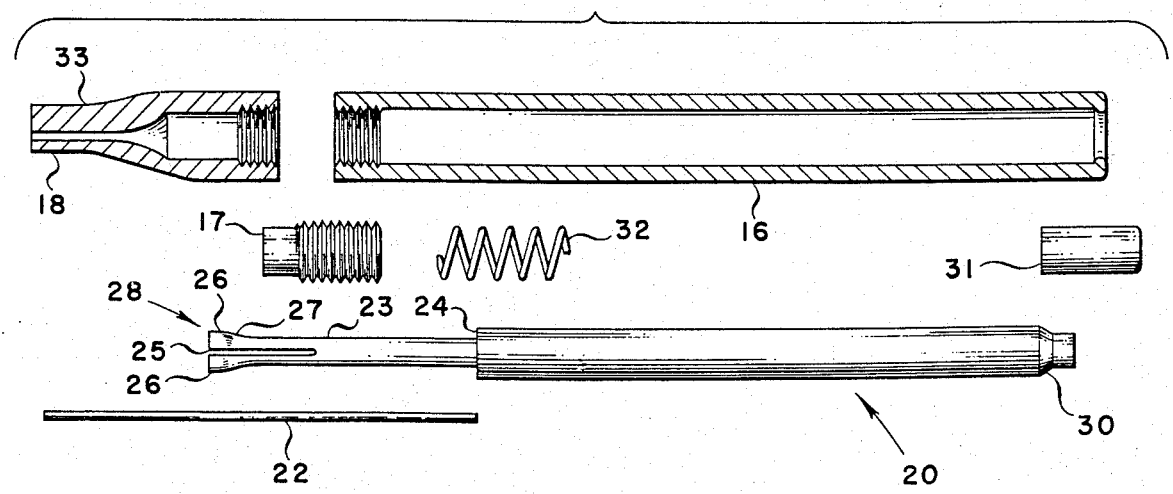
FIG. 3 is an exploded view of the same pencil shown in FIG. 2 to show the assembly of the several components thereof.

Referring more particularly to the drawings, 10 designates an oblong, cylindrical shaped instrument or pencil slidably mounted in a sleeve 11 pivotally secured, as at 12, to a support 13. The support 13 is an anvil formed or otherwise provided with an outer face 14 configured to abut the surface of a metal specimen 15 under test or to be ultimately monitored.

The pencil 10 is composed of an outer cylindrical tube 16 open at both ends and internally threaded at one end to receive and secure an externally threaded connector 17 adapted to extend therefrom and threadably connect tapered nozzle 18. Externally the tube 16 is inscribed with calibrations 19 indicating the angle of inclination $\alpha$ of the pencil 10 as established by the length L of the pencil 10 between the pivot 12 and the pointed or tapered end of the pencil 10 and the height H established by the shortest distance between the pivot 12 and the surface of the specimen 15.

A center tube 20 is carried internally of the outer tube 16. This tube 20 has a thin wall at one end forming a container 21 for the storage of multiple sticks or rods 22 of brittle, frangible material, such as glass, preferably tubular, and of substantially reduced outer diameter 23 less than the internal diameter of the connector 17 at the other end with a step 24 formed between such end portions. The wall of the reduced diameter portion 23 is substantially thicker than that of the container end 21 defining an internal diameter substantially equal to that of each glass rod or tube 22. In addition this wall on the portion 23 is split longitudinally as at 25 to produce a plurality of radial, spring fingers 26 each terminating in an outwardly sloped segment 27. The several segments 27 have outer surfaces which coact one with the other to form a split collar 28, which when compressed has a diameter slightly larger than the internal diameter of the connector 17 for reasons to become apparent.

Internally the wall of the center tube 20 is tapered, as at 29, whereby the internal diameter of the container 21 gradually reduces to that of the end portion 23. Thus only one tube 22 can pass at a time from the container 21 into the end portion 23 when the pencil 10 is held in the vertical position. The center tube end portion 23 is designed and adapted to be inserted into the connector 17 and the connector 17 threaded into, so as to project beyond, the outer tube 16 and receive the nozzle 18 thereon, as described. The other end of the center tube 20 terminates in a tapered end 30 adapted to receive a closure cap 31 which is normally retained thereon by clamping pressure but readily removed by an outward pull.

A compression spring 32 is provided on and around the center tube end portion 23 prior to its insertion into the connector 17 whereby to act against the step 24 and the connector 17 tending to maintain them in spaced relation. Thus, with the pencil 10 assembled as above, and held in a generally upright or vertical position pressure applied to the cap 31 forces the center tube 20 to slide within the outer tube 16 against the normal action of the spring 32. The spring is thereby fully compressed between the step 24 and the connector 17 and the fingers 26 extended outwardly of the connector 17 into the nozzle 18. At the same time a glass tube 22 within the fingers 26 is gripped thereby due to the radial pressure applied by the connector 17 on the fingers 26 so that this glass tube 22 moves into the nozzle 18. When the pressure applied to the cap 31 is thereafter released, the center tube returns to its original position by the normal action of the springs 32.

The sloped surfaces of the several segments 27 permit the split collar 28 to be compressed by the connector 17 during the return operation of the center tube 20. The internally tapered nozzle 18 accommodates the extension of the fingers 26 and glass tube 22 as above described, the outer end of the nozzle 18 being accurately designed to an internal diameter substantially equal to that of each glass tube 22 to thereby retain the projected tube during the return operation of the center tube 20.

The compression of the spring 32 and hence the movement of the center tube 20 in the outer tube 16 i.e., the stroke, is precisely established. The length of tube 22 extending beyond the end of the nozzle 18 is thereby determined. These values are built into the pencil 10 for example as follows:

1. in the case of a 0.3 mm outside diameter glass tube 22, the stroke is established to extend the end of the tube 22 two (2) mm so that when positioned at an angle of 45° relative to the face 14 of a steel specimen 15 a stress pulse of 0.08 kg is produced for a rising time of 0.15 micro-seconds.

2. in the case of a 0.5 mm outer diameter glass tube 22, extension of two (2) mm and inclined at an angle of 45° relative to the surface of a steel specimen a stress pulse of 0.30 kg is produced for a rising time of 0.30 micro-seconds.

In order to produce the simulated acoustic emission as set forth above, it is only necessary to push the protruded portion of the tube 22 slowly against the test specimen 15 at the tip of the tube 22 until it breaks. Since the mode of the stress pulse (acoustic emission) generated depends on the angle $\alpha$ such angle $\alpha$ must be precisely controlled, if a consistent and reproducible stress pulse is to be obtained. To this end, the support 13 is provided in the form of an anvil which in conjunction with the calibrations 19 on the pencil permit such precise position to be controlled.

It is noted that the wall of the nozzle 18 is enlarged or thickened as at 33 on the side thereof remote from the specimen 15 to assure withstanding the force applied when the rod 22 is pressed against the specimen 15 and broken. Also a protective shield 34 is mounted on and around the nozzle 18 as for example by a claming ring 35 to overlie the projecting rod 22 and deflect it when broken as above described.

While the invention has been hereinabove illustrated and described in what it believed to be its best and most practical form under present-day conditions, it is recognized that under other conditions this form would be modified. No attempt has been made to specifically incorporate any of such other forms in this disclosure in the interest of clarity of the total invention concept. The claims are relied upon to cover these other forms generally.

What is claimed:

1. An instrument adapted to generate a stress pulse on a localized area of a metal specimen simulating the acoustic emission which emanates from an actual crack in said specimen comprising:

an outer cylindrical tube tapered at its forward end;
a core mounted for limited sliding movement in said tube;
a gripping element carried by said core at its forward end adjacent said tapered tube end and adapted to secure a frangible element when said core moves toward said tapered tube end and to release said frangible element when said core moves toward the aft end of said tube, whereby said frangible element is moved a predetermined distance toward and extended a predetermined distance beyond said tapered tube end; and
an angularly adjustable support carried by said tube for abutment against said specimen to dispose said frangible element when extended as aforesaid at a preselected angle relative to the surface of said specimen whereby a force applied thereon moves the frangible element against said specimen until it breaks.

2. The instrument of claim 1 wherein said tapered tube end includes a thickened wall on the side thereof remote from said specimen when said support abuts the specimen as aforesaid.

3. The instrument of claim 1 including a shield carried by said tapered tube end overlying the frangible element when extended as aforesaid.

4. The instrument of claim 1 wherein said core terminates beyond the aft end of said tube and includes a compression spring disposed between said core and said tapered tube end and operative to control the limited sliding movement of the tube as aforesaid.

5. The instrument of claim 1 wherein said core includes a center tube terminating at its aft end in a relatively large inner and outer diameter portion constituting a container for the storage of multiple said frangible elements and terminating at its forward end in a relatively small inner and outer diameter portion forming a passage sized to accommodate only one said frangible element at a time, the internal surfaces of said diameter portions merging in a smooth, uninterrupted transition surface whereby a single said frangible element moves from said container into said small diameter portion when said instrument is disposed in an upright position.

6. The instrument of claim 1 wherein said support includes a sleeve slidably mounted on said outer tube and an anvil pivotally secured to said sleeve, said anvil having an outer surface adapted to contact said specimen.

7. The instrument of claim 6 wherein said outer tube includes calibrations inscribed thereon adapted for coaction with said sleeve to indicate the angle of inclination of said outer tube to said specimen.

* * * * *